United States Patent [19]
Church

[11] Patent Number: 6,092,525
[45] Date of Patent: Jul. 25, 2000

[54] SPINAL IMMOBILIZATION DEVICE

[76] Inventor: Steve Church, 4521 Hancock Dr., Midland, Mich. 48642

[21] Appl. No.: 08/791,455

[22] Filed: Jan. 27, 1997

[51] Int. Cl.[7] .................................................. A61B 19/00
[52] U.S. Cl. ........................... 128/869; 128/872; 128/876
[58] Field of Search ..................... 128/845, 846, 128/869, 874, 875, 876; 5/636

[56] References Cited

U.S. PATENT DOCUMENTS

| | | | |
|---|---|---|---|
| 438,639 | 10/1890 | Rupelye | 128/872 |
| 3,276,430 | 10/1966 | Murcott | 128/874 |
| 3,323,150 | 6/1967 | Rehder | 128/875 |
| 4,653,131 | 3/1987 | Diehl | 128/872 |
| 4,922,562 | 5/1990 | Allred | 128/870 |
| 5,010,900 | 4/1991 | Auchinleck | 128/856 |
| 5,275,178 | 1/1994 | Roberson | 128/869 |
| 5,435,323 | 7/1995 | Rudy | 128/870 |
| 5,505,162 | 4/1996 | Fleischer | 119/792 |

*Primary Examiner*—Michael A. Brown

[57] ABSTRACT

A spinal immobilization panel (panel) adapted to be attached to a spinal immobilization backboard (backboard) and to secure an injured person to the backboard. The panel comprises a substantially rectangularly shaped flexible material, at least one short strapping member (short strap) disposed across the width of the rectangularly shaped flexible material and having two ends provided with fastening means adapted to be attached to a backboard and a pair of spaced-apart long strapping members (long straps) disposed across the length of the rectangularly shaped material. Each of the pair of long strapping members has two ends provided with fastening means adapted to be attached to a backboard.

16 Claims, 3 Drawing Sheets

SPINAL IMMOBILIZATION DEVICE

BACKGROUND OF THE INVENTION

This invention relates to a device for the spinal immobilization of a patient and more particularly to a flexible spinal immobilization device.

Splints of the type to which the present invention relates are frequently used in emergency situations such as automobile accidents in which the patient suffered injury or suspected injury to the back or neck areas. The handling of such injured patients requires special care in order to avoid further injury to the patient during the patient's extrication from the site of the accident and transfer to a hospital. Conventional stretchers do not meet the need of such patients as it is often necessary to extricate the patient from a wrecked automobile, building site or some similar location where the patient can not be disposed easily onto a stretcher. In these cases, it is conventional to endeavor to immobilize the spinal column of the patient.

Devices for spinal immobilization are known in the art. See, for example, U.S. Pat. Nos. 4,211,218; 4,936,296;4,584,729; 5,568,662; and 5,515,869. The devices described in these patents are complicated and cumbersome to use.

It would be desirable to provide a spinal immobilization device which is simple and easy to use.

SUMMARY OF THE INVENTION

In a first aspect, this invention is a spinal immobilization panel (panel) which is adapted to be attached to a spinal immobilization backboard (backboard) and to secure an injured person to the backboard, the panel comprising a substantially rectangularly shaped flexible material, at least one short strapping member disposed across the width of the rectangularly shaped flexible material and having two ends provided with fastening means adapted to be attached to a backboard; and a pair of spaced-apart long strapping members disposed across the length of the rectangularly shaped material, each of said long strapping members having two ends provided with fastening means adapted to be attached to a backboard.

In a second aspect, this invention is a spinal immobilization device comprising an immobilization backboard (backboard) and an immobilization panel (panel) comprising a substantially rectangularly shaped flexible material, at least one short strapping member disposed across the width of the rectangularly shaped material and having two ends provided with fastening means adapted to be attached to a backboard; and a pair of spaced-apart long strapping members disposed across the length of the rectangularly shaped material, each of said long strapping members having two ends provided with fastening means adapted to be attached to a backboard.

SHORT DESCRIPTION OF THE DRAWINGS

DETAILED DESCRIPTION OF THE INVENTION

Figure 1:
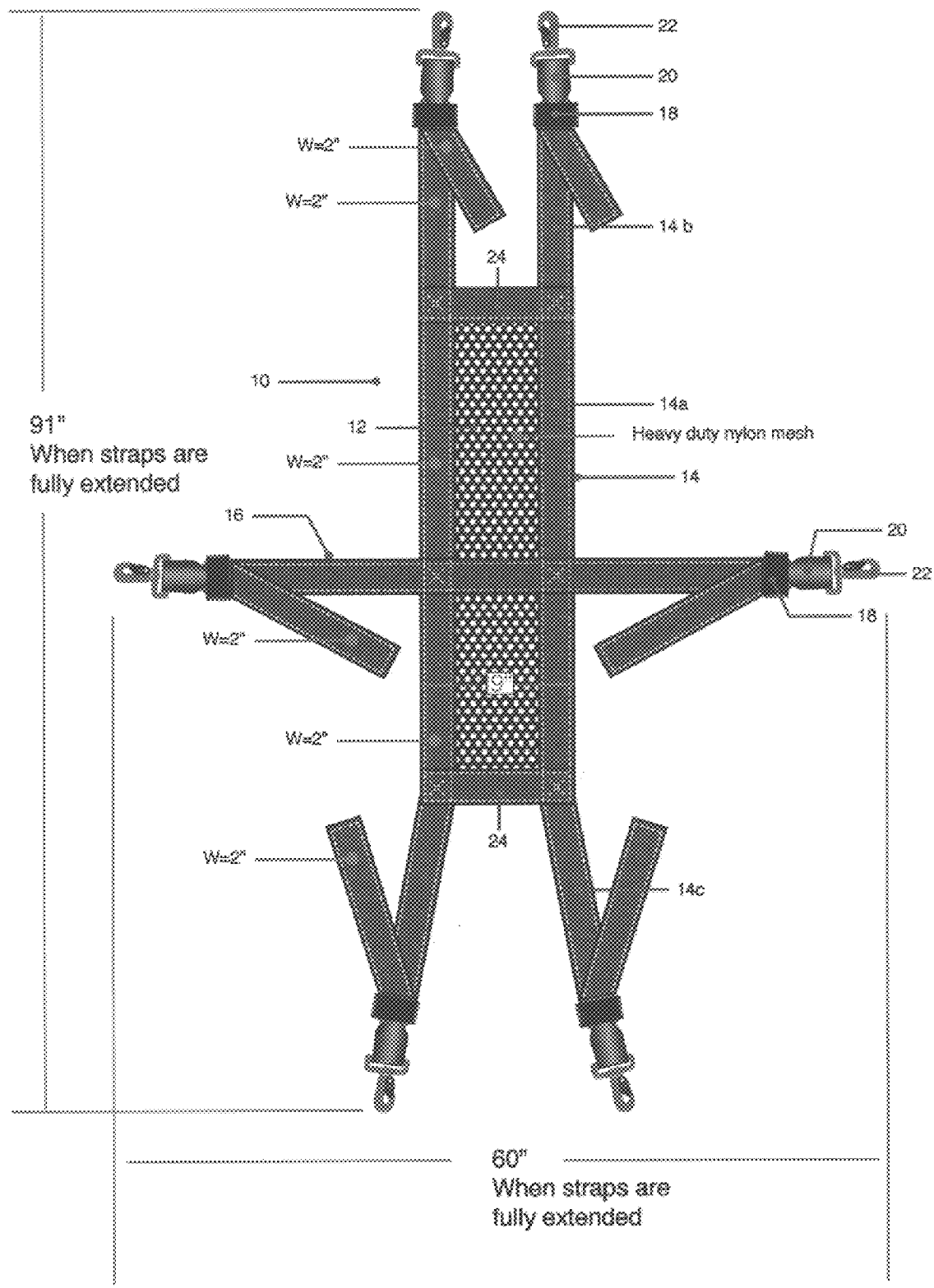
FIG. 1 is a top view of the immobilization device the present invention.

Referring now to the drawings, FIG. 1 shows a spinal immobilization panel (panel), generally represented by reference numeral 10, comprising a rectangularly shaped flexible material 12 having a pair of long strapping members (straps) 14 extending across its length and attached along its two long edges and one short strapping member (strap) 16 extending across its width. Preferably, rectangularly shaped flexible material 12 is provided with reinforcing fabric 24, attached along its edges. Reinforcing fabric 24 can be in the form of a webbing and can comprise the parts of the straps which are attached along the edges of flexible material 12. Straps 14 and 16 are provided with fastening means 20 at their free ends. Strap 16 is positioned at or just below where the chest of a patient would be when the patient is secured by the panel to a backboard.

Preferably, the rectangularly shaped flexible material is about 9 inches wide and about 29 inches long. The short strap is preferably about 14 to about 17 inches, more preferably, about 14½ inches, from the top short edge of the rectangularly shaped material. By the term "top short edge" is meant the short edge closest to the head of a patient which is secured by the panel to a backboard.

Figure 2:
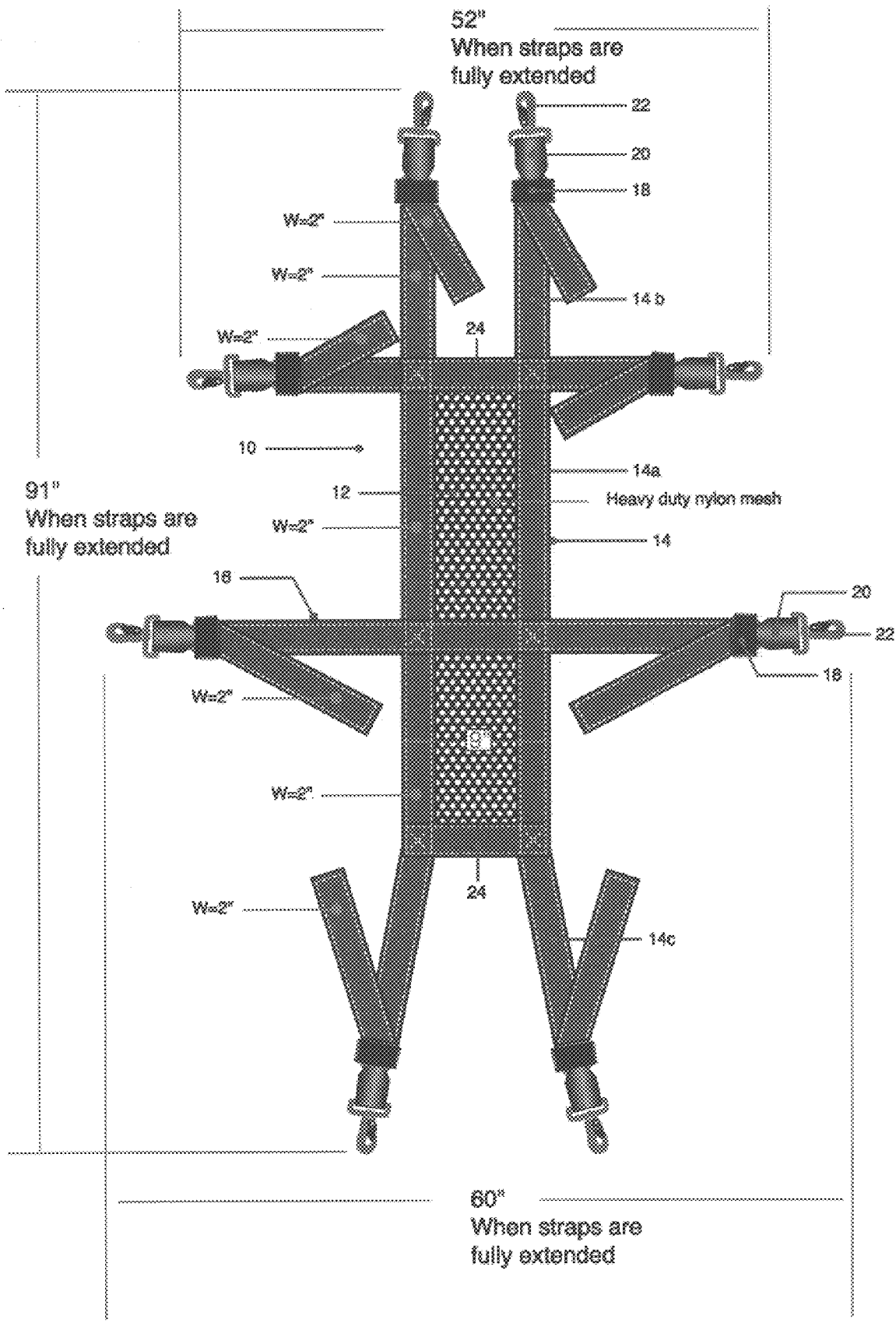
FIG. 2 is a top view of another embodiment of the present invention.

FIG. 2 shows an immobilization panel which is identical to that shown in FIG. 1, except that it comprises a pair of short straps 16. One of the straps is positioned at or just below where the chest of a patient would be when the patient is secured by the panel to a backboard, and the second strap 16 is positioned at or below the hips of the patient.

Figure 3:
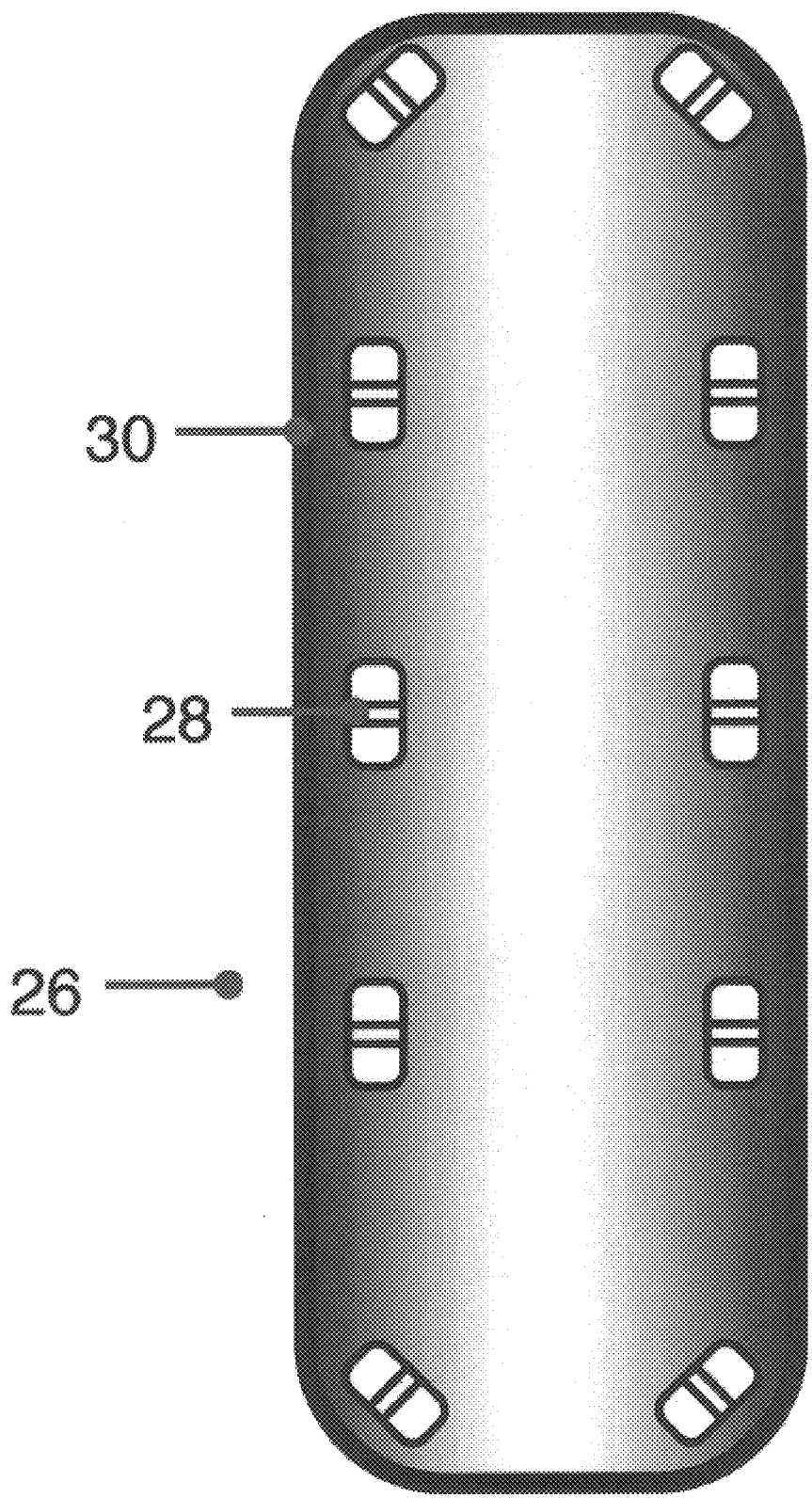
FIG. 3 is a top view of a conventional immobilization backboard.

FIG. 3 shows a conventional spinal immobilization backboard, generally represented by reference numeral 26. Backboard 26 is provided with a series of slots 28 along its edges. Each slot is provided with a pin 30.

Backboards which are suitable for use in the practice of the present invention include any of the backboards known in the art. The backboards are full length boards (typically 6 feet long) and are sized (16 inches) to be narrower than the width of a typical person. The boards are typically made of hard wood material or metal. Some boards are made of wood, plastic, fiberglass or composites. Composites comprise a resin matrix and fiber reinforcements.

Composites are known in the art and reference thereto is made for the purposes of the present invention. Some backboards are made of injection molded plastic boards with or without fiber reinforcements. The fiber-reinforced, resin transfer molded, composite boards can carry up to 700 pounds without cracking.

The backboard is provided with at least two pairs of slots disposed along its edges and adapted to receive the strapping members of the spinal immobilization panel when the panel is attached to the backboard to secure an injured person to the backboard. Preferably, the slots along one edge are aligned with the corresponding slots along the opposite edge of the backboard. In the preferred embodiment of the present invention, each slot is provided with a pin which is securely attached to the inner sides of the slots as shown in FIG. 3.

Flexible materials which can be used in the practice of the present invention for making the panel include woven and non-woven fabrics made of thermoplastic, thermosetting or naturally occurring materials. Examples of such materials include nylon netting, nylon webbing and the like.

The straps may be formed of one continuous length of strap material or may be formed of three separate parts attached to each other to form a single strap. Preferably, as shown in FIGS. 1 and 2, long straps 14 comprise parts 14a, 14b and 14c where part 14b is attached to one free end of part 14a and part 14c is attached to the other free end of part 14a, in alignment or slightly out of alignment (about 180 to about 195°), as shown in FIGS. 1 and 2. The straps can be made of polyester, nylon, polypropylene or other thermoplastic materials. Preferably, the straps are made of polypropylene or nylon straps.

Attached to the free ends of each strap are fastening means 20. Suitable fastening means include conventional type interlocking buckles having a male and a female member. The free ends of each strap have either a male member or a female member of a buckle. The male or female member of the buckle attached to the straps is adapted to interlock with the female or male member of the buckle which is attached to the backboard.

The straps would have the conventional structure for lengthening or shortening the straps depending on the girth of the injured person. Packing loops may be provided to store the straps when not being used. Preferably, as shown in FIGS. 1 and 2, fastening means 20 comprises a swivel snap 22 which is adapted to snap to the pin securely positioned in the slot of the backboard. The swivel snap 22 is attached to the free ends of each strap by means of an adjuster 18 which is adapted to adjust the length of the strap.

All of the materials employed in making the spinal immobilization device of the present invention, such as the flexible rectangularly shaped material, straps, swivel snaps and adjusters are commercially available.

When using the spinal immobilization panel or device of the present invention, the injured person is placed on the backboard and securely immobilized by the spinal immobilization panel which is adapted to extend about the body of the injured person and securely attach to the spinal immobilization backboard.

I claim:

1. A spinal immobilization panel adapted to be attached to a spinal immobilization backboard and to secure an injured person to the backboard, the panel comprising a substantially rectangularly shaped flexible material selected from the group consisting of woven thermoplastic fabrics, woven thermosetting fabrics non-woven thermoplastic fabrics and non-woven thermosetting fabrics, two short straps disposed across the width of the rectangularly shaped flexible material, one of said straps being positioned at or just below where the chest of the patient would be when the patient is secured by the panel to the backboard, and the other of said straps being positioned at or below the hips of the patient when the patient is secured by the panel to the backboard, each of said straps having two ends provided with fastening means adapted to be attached to the backboard; and a pair of spaced-apart long straps disposed across the length of the rectangularly shaped material, each of said long straps being attached along each of the two long edges of the rectangularly shaped material and having two ends provided with fastening means adapted to be attached to the backboard.

2. The panel of claim 1 wherein the pair of long straps are attached along the two long edges of the rectangularly shaped flexible material.

3. The panel of claim 1 wherein the rectangularly shaped flexible material is about 9 inches wide and about 29 inches long.

4. The panel of claim 1 wherein the short strap is about 14 to about 17 inches from the top short edge of the rectangularly shaped material.

5. The panel of claim 1 wherein the short strap is about 14½ inches from the top short edge of the rectangularly shaped material.

6. The panel of claim 1 wherein the flexible material is made of nylon netting or nylon webbing.

7. The panel of claim 1 wherein the long straps are formed of one continuous length of strap material or of three separate straps attached to each other to form a single strap.

8. The panel of claim 1 wherein the long straps are each formed of three separate short straps comprising a middle strap and one strap attached at each end of the middle strap, in alignment or slightly out of alignment.

9. The panel of claim 1 wherein the straps are made of polyester, nylon or polypropylene.

10. The panel of claim 1 wherein the fastening means comprises a swivel snap which is adapted to snap to a pin securely positioned in the slot of a backboard and an adjuster which is adapted to adjust the length of the strap.

11. A spinal immobilization device comprising a spinal immobilization backboard and an immobilization panel adapted to be attached to the backboard and to secure an injured person to the backboard, the panel comprising a substantially rectangularly shaped flexible material selected from the group consisting of nylon netting and nylon webbing; two short straps disposed across the width of the rectangularly shaped flexible material, one of said straps being positioned at or just below where the chest of the patient would be when the patient is secured by the panel to the backboard, and the other of said straps being positioned at or below the hips of the patient when the patient is secured by the panel to the backboard, each of said straps having two ends provided with fastening means adapted to be attached to the backboard; and a pair of spaced-apart long straps disposed across the length of the rectangularly shaped flexible material, each of said long straps being attached along each of the two long edges of the rectangularly shaped material and having two ends provided with fastening means adapted to be attached to the backboard.

12. The device of claim 11 wherein the pair of long straps are attached along the two long edges of the rectangularly shaped flexible material.

13. The device of claim 11 wherein the rectangularly shaped flexible material is about 9 inches wide and about 29 inches long.

14. The device of claim 11 wherein the short strap is about 14 to about 17 inches from the top short edge of the rectangularly shaped material.

15. The device of claim 11 wherein the short strap is about 14½ inches from the top short edge of the rectangularly shaped material.

16. A spinal immobilization device comprising a spinal immobilization backboard and an immobilization panel adapted to be attached to the backboard and to secure an injured person to the backboard, the panel comprising a substantially rectangularly shaped flexible material; two short straps disposed across the width of the rectangularly shaped flexible material, one of said straps being positioned at or just below where the chest of the patient would be when the patient is secured by the panel to the backboard, and the other of said straps being positioned at or below the hips of the patient when the patient is secured by the panel to the backboard, each of said straps having two ends provided with fastening means adapted to be attached to the backboard; and a pair of spaced-apart long straps disposed across the length of the rectangularly shaped flexible material, each of said long straps being attached along each of the two long edges of the rectangularly shaped material and having two ends provided with fastening means adapted to be attached to the backboard.

* * * * *